US010369061B2

(12) United States Patent
Jönegren et al.

(10) Patent No.: US 10,369,061 B2
(45) Date of Patent: Aug. 6, 2019

(54) ABSORBENT PRODUCT COMPRISING INLET MATERIAL

(71) Applicant: SCA Hygiene Products AB, Göteborg (SE)

(72) Inventors: Åsa Jönegren, Göteborg (SE); Pia Kalentun, Göteborg (SE); Susanna Edrud, Göteborg (SE); Morgan Hansson, Göteborg (SE); Susanne Andersson, Göteborg (SE)

(73) Assignee: ESSITY HYGIENE AND HEALTH AKTIEBOLAG, Göteborg (SE)

( * ) Notice: Subject to any disclaimer, the term of this patent is extended or adjusted under 35 U.S.C. 154(b) by 0 days.

(21) Appl. No.: 15/580,883

(22) PCT Filed: Jun. 10, 2015

(86) PCT No.: PCT/SE2015/050671
§ 371 (c)(1),
(2) Date: Dec. 8, 2017

(87) PCT Pub. No.: WO2016/200300
PCT Pub. Date: Dec. 15, 2016

(65) Prior Publication Data
US 2018/0161218 A1 Jun. 14, 2018

(51) Int. Cl.
A61F 13/15 (2006.01)
A61F 13/47 (2006.01)
(Continued)

(52) U.S. Cl.
CPC .... A61F 13/53713 (2013.01); A61F 13/4704 (2013.01); A61F 13/476 (2013.01);
(Continued)

(58) Field of Classification Search
CPC .......... A61F 13/15; A61F 13/47; A61F 13/53; A61F 13/51; C08L 77/00; A01K 23/00; A47L 13/17
See application file for complete search history.

(56) References Cited

U.S. PATENT DOCUMENTS 5,611,790 A 3/1997 Osborn, III et al.
5,817,081 A 10/1998 LaVon et al.
(Continued)

FOREIGN PATENT DOCUMENTS

CA 2019455 A1 11/1991
GB 2055586 A 3/1981
(Continued)

OTHER PUBLICATIONS

Japanese Office Action issued in Japanese patent application No. 2017-563992, dated Dec. 3, 2018 (4 pages) and its English-language translation thereof (4 pages).
(Continued)

Primary Examiner — Tatyana Zalukaeva
Assistant Examiner — Ilya Y Treyger
(74) Attorney, Agent, or Firm — Drinker Biddle & Reath LLP

(57) ABSTRACT

An absorbent product includes a liquid pervious topsheet, a liquid impervious backsheet and an absorbent core enclosed between the liquid pervious topsheet and liquid impervious backsheet. The absorbent product has in its longitudinal direction a crotch part and two end parts. The absorbent product includes at least in its crotch part an inlet material having a plurality of openings. The plurality of openings in the inlet material are formed from a plurality of slits extending in the transversal direction of the absorbent product by expanding the continuous inlet material in the longitudinal direction of the absorbent product. The liquid inlet material
(Continued)

has in its transversal direction of the absorbent product a central region and two edge regions. The openings are located in the central region so that the central region of the material with the plurality of openings has a lesser degree of elasticity than the edge regions.

23 Claims, 3 Drawing Sheets

(51) Int. Cl.
| | |
|---|---|
| A61F 13/537 | (2006.01) |
| A61F 13/475 | (2006.01) |
| A61F 13/476 | (2006.01) |
| A61F 13/49 | (2006.01) |
| B32B 5/04 | (2006.01) |
| B32B 3/10 | (2006.01) |
| B32B 3/26 | (2006.01) |
| B32B 5/02 | (2006.01) |
| B32B 5/18 | (2006.01) |
| B32B 5/24 | (2006.01) |
| A61F 13/53 | (2006.01) |
| A61F 13/51 | (2006.01) |
| B32B 37/12 | (2006.01) |
| A61F 13/45 | (2006.01) |

(52) U.S. Cl.
CPC .... *A61F 13/4755* (2013.01); *A61F 13/49017* (2013.01); *B32B 3/10* (2013.01); *B32B 3/266* (2013.01); *B32B 5/022* (2013.01); *B32B 5/04* (2013.01); *B32B 5/18* (2013.01); *B32B 5/245* (2013.01); *A61F 2013/4587* (2013.01); *A61F 2013/4708* (2013.01); *B32B 5/24* (2013.01); *B32B 37/1292* (2013.01); *B32B 2307/726* (2013.01); *B32B 2307/7265* (2013.01); *B32B 2307/73* (2013.01); *B32B 2437/02* (2013.01); *B32B 2555/02* (2013.01)

(56) References Cited

U.S. PATENT DOCUMENTS

| | | | |
|---|---|---|---|
| 5,868,724 | A | 2/1999 | Dierckes, Jr. et al. |
| 2003/0114811 | A1 | 6/2003 | Christon et al. |
| 2010/0036351 | A1 | 2/2010 | Larson et al. |
| 2011/0004175 | A1 | 1/2011 | Veith |
| 2012/0095426 | A1 | 4/2012 | Visscher et al. |
| 2013/0012898 | A1 | 1/2013 | Bergendahl et al. |
| 2013/0144241 | A1 | 6/2013 | Persson et al. |
| 2014/0295134 | A1 | 10/2014 | Wood et al. |
| 2014/0303581 | A1 | 10/2014 | Karlsson |
| 2015/0133883 | A1 | 5/2015 | Cardin et al. |
| 2016/0074237 | A1 | 3/2016 | Rosati et al. |
| 2017/0027778 | A1 | 2/2017 | Stridfeldt et al. |
| 2018/0338869 | A1 | 11/2018 | Jonegren et al. |

FOREIGN PATENT DOCUMENTS

| | | | |
|---|---|---|---|
| GB | 2310606 | A | 9/1997 |
| JP | 2000-505339 | A | 5/2000 |
| JP | 2010-214049 | A | 9/2010 |
| WO | WO-93/01781 | A1 | 2/1993 |
| WO | WO-95/00091 | A1 | 1/1995 |
| WO | WO 99/01098 | * | 7/1997 |
| WO | WO-97/31601 | A1 | 9/1997 |
| WO | WO-98/13003 | A1 | 4/1998 |
| WO | WO-99/01098 | A1 | 1/1999 |
| WO | WO-2006/102974 | A1 | 10/2006 |
| WO | WO-2009/105000 | A1 | 8/2009 |
| WO | WO 2011/115537 | A1 * | 3/2010 |
| WO | WO-2011/056205 | A1 | 5/2011 |
| WO | WO-2011/115537 | A1 | 9/2011 |
| WO | WO 2014/085974 | A1 * | 12/2012 |
| WO | WO-2013/180937 | A1 | 12/2013 |
| WO | WO-2014/085974 | A1 | 6/2014 |
| WO | WO-2015/094068 | A1 | 6/2015 |

OTHER PUBLICATIONS

Extended European search report issued in European patent application No. 15895076.6, dated Jan. 8, 2019.
International Preliminary Report on Patentability dated Dec. 12, 2017 issued in corresponding International application No. PCT/SE2015/050672 (8 pages).
Examination report No. 1 dated Jan. 22, 2018 issued in corresponding Canadian patent application No. 2015398532 (3 pages).
Extended European search report issued in European patent application 15 89 5077.4, dated Nov. 13, 2018.
Office Action issued in U.S. Appl. No. 15/580,851, dated Jan. 3, 2019, with double-patenting rejections on pp. 8 and 9.
Colombian Office Action Oficio N° 980 issued in Colombian patent application No. NC2017/0012395 dated Mar. 13, 2019 (9 pages) and its partial English-language translation thereof (6 pages).
Mexican Office Action No. Folio 7020 issued in Mexican patent application No. MX/a/2017/015026 dated Feb. 5, 2019 (3 pages) and its partial English-language translation thereof (2 pages).

* cited by examiner

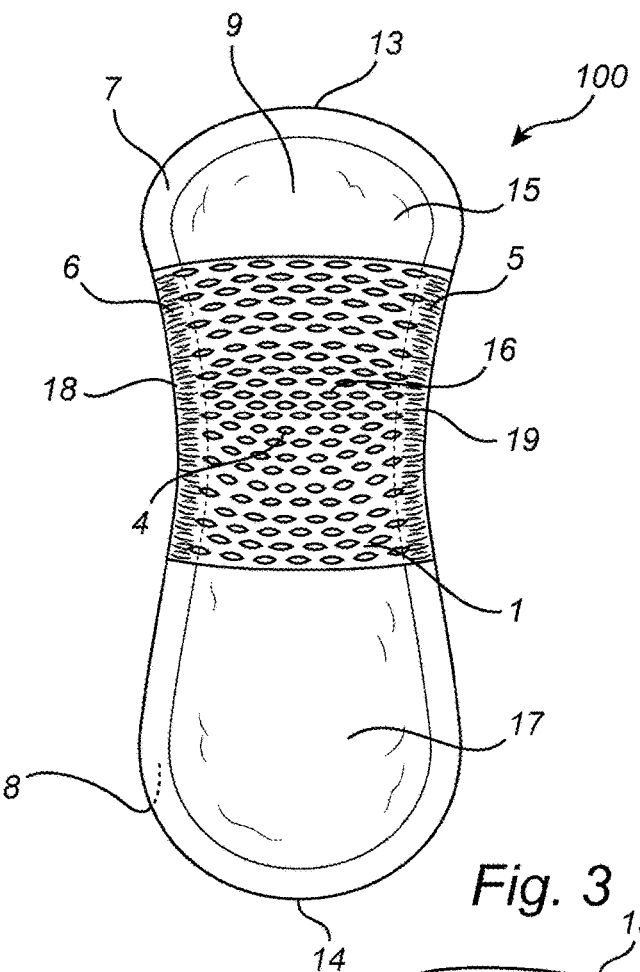
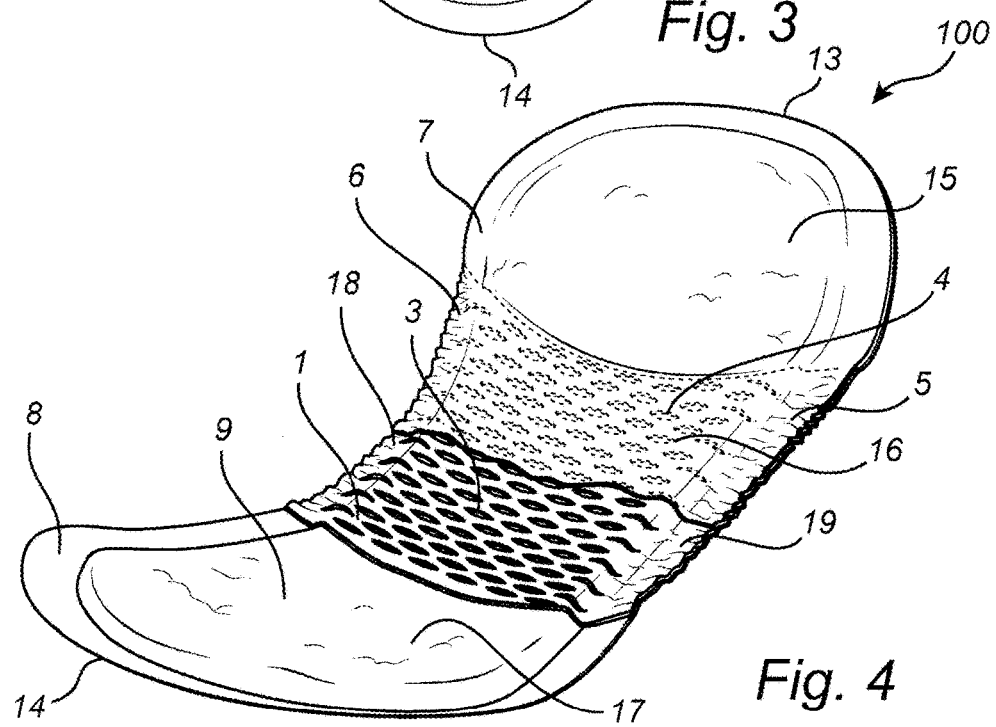

ABSORBENT PRODUCT COMPRISING INLET MATERIAL

CROSS-REFERENCE TO PRIOR APPLICATION

This application is a § 371 National Stage Application of PCT International Application No. PCT/SE2015/050671 filed Jun. 10, 2015, which is incorporated herein in its entirety.

TECHNICAL FIELD

The present disclosure relates to an absorbent product including a liquid pervious topsheet, a liquid impervious backsheet and an absorbent core enclosed between the liquid pervious topsheet and liquid impervious backsheet. The absorbent product has in its longitudinal direction a crotch region and two end regions wherein at least the crotch region includes an inlet material having a plurality of openings.

BACKGROUND

For absorbent products such as incontinence shields there are high requirements that they are discreet, soft and comfortable to wear and at the same time have a reliable security against leakage.

Incontinence shields have to be sized and configured to fit in the limited space available in the crotch portion of the underwear so the products are by necessity designed with a relatively small width. For this reason, a particular problem with such products is that they may leak at the side edges, before the full absorption capacity of the product has been utilized.

Side leakage may occur as a consequence of absorbed fluid being dispersed equally fast in all directions from the point where the fluid enters the product. This will lead to the fluid escaping the product at the side edges before being distributed to the end portions. Another cause of side leakage may be when the intake capacity of the product is insufficient to allow all fluid that is exuded onto the product to directly enter inside the product. Instead, the fluid will flow on the top sheet and out over the side edges where it can leak out and soil the wearer's clothing.

The urine fluid is normally not exuded in a steady flow but as sudden gushes of relatively large volume under high pressure and during a very short time period.

Accordingly, it would be desirable if the incontinence shield was able to receive and contain the emitted fluid with corresponding speed.

Although the prior art liquid inlet material may alleviate the side leakage problem to some extent, there is still a need for further improvements of the side leakage security for the kind of absorbent article that is worn in the crotch portion of an undergarment.

DETAILED DESCRIPTION OF PARTICULAR EMBODIMENTS

In accordance with the disclosure, there is provided an absorbent product having improved leakage security and fit.

The absorbent product including a liquid pervious topsheet, a liquid impervious backsheet and an absorbent core enclosed between the liquid pervious topsheet and liquid impervious backsheet. The absorbent product has in its longitudinal direction a crotch part and two end parts wherein the absorbent product at least in its crotch part includes an inlet material having a plurality of openings. The plurality of openings in the inlet material is formed from slits extending in the transversal direction of the absorbent product that have been expanded in the longitudinal direction of the absorbent product. The liquid inlet material has in the transversal direction of the absorbent product a central region and two edge regions. The openings are located in the central region so that the central region of the material with the plurality of openings has a lesser degree of elasticity than the edge regions.

An effect of having a central region of the material with slits and edge regions of the material without slits will, after the material has been extended so that openings have been formed from the slits, lead to different elasticity in different regions of the material. The openings in the central region of the inlet material will give the material in this region a lower degree of elasticity than the edge regions free from openings. A greater degree of elasticity of the edge regions than in the central region of the crotch part is advantageous since the edge region of the inlet material will function as leg elastics and has a greater elasticity than the central part of the inlet material. The absorbent product may also obtain a bowl shape in the crotch region as a result of an elastic contraction of the edge regions of the inlet material having a greater elasticity than the central region of the inlet material.

Another advantage with edge regions without openings is that the edges may function also as liquid edge barriers decreasing the risk for side leakage.

One advantage with openings in the central region of the inlet material is that the liquid inlet into the product is improved. An alternative way of creating openings in a material would be to punch/perforate. However, a slitting method is advantageous over punching/perforating since no material is cut out from the web. This saves money due to less waste of material and also improves the handling in the production process by avoiding having a lot of small pieces cut out from the material that may otherwise contaminate both the process equipment and the final product.

The inlet material has to be able to absorb sudden gushes of relatively large volume during a very short time period and with the present disclosure it is possible to provide an inlet material with a plurality of openings and leg elastic material, of the same continuous material sheet.

Since the edge regions extending in the longitudinal direction of the absorbent product will function as leg elastics and support in creating a bowl shape in the crotch area, there is no need for a separate material sheet/element to create the leg elastics. The inlet material and the material for the leg elastics are the same continuous material sheet.

The inlet material may be located between the top sheet and the absorbent core or the inlet material may be the liquid permeable top sheet or part thereof.

The inlet material may have a greater width than the absorbent core. If the absorbent core includes more than one layer, the inlet material may have a greater width than at least one of the layer in the absorbent core.

The central region of the inlet material may have a greater width, at least in the crotch part of the absorbent product, than the absorbent core. An advantage by having a greater width of the central region of the inlet material than the absorbent core, is that the plurality of openings extends over the absorbent core and also a part outside the absorbent core in the transversal direction of the product so there will be a part of the absorbent product located in the transversal direction between the absorbent core and the leg elastic region which is the edge region, with not so much material (no absorbent core and an inlet material with a plurality of openings), and this part will, due to a hinge effect, make it easier for the edge region with greater elasticity to retract the absorbent product into a bowl shaped product.

The inlet material has in the transversal direction of the absorbent product two edge regions and a central region between the edge regions and the edge region may be at least 5 mm along the whole side edge of the product. Otherwise, it will be more difficult for the edge regions to function as leg elastics and retract the absorbent product into a bowl shape in the crotch region.

The width of the opening in the longitudinal direction of the absorbent product may be 0.2 to 3.0, or 0.5 to 1.0 of the length of the opening in the transversal direction.

The inlet material may have been extended 30% to 200% from the original length of the unexpanded inlet material.

The inlet material may be hydrophobic. An advantage with a hydrophobic material is that hydrophobic edge regions free of openings will function as liquid barriers and will decrease the risk for edge leakage. Also, a hydrophobic inlet material can be preferred from a skin care view since a dry surface close to the user's skin may decrease the risk for bacterial growth and skin irritations.

The liquid inlet material may be of a foam material. An advantage to have a foam material as liquid inlet material is that such a product is experienced as soft and is also aesthetically pleasing for many users. The ability of a foam material to spring back, to return to substantially its original form after having been exposed to outer loading is also an important property. Since the foam material has a continuous structure, it exhibits good pliability and also ability to spring back following outer loading.

Foam material may have an open cell structure or a closed cell structure. Foam used as a liquid-receiving foam layer in an absorbent product, is often foam with open cells so that the liquid easily enters the foam and also the absorbent core below. However, with the slit openings it is possible also to use foam having closed cells. An advantage with foam including closed cells is that the liquid will not easily enter the foam structure itself, and therefore the foam material will be kept in a more dry condition than foam with open pore cells that are connected with each other.

The inlet material may also be a fibrous material, for example a nonwoven or laminate thereof.

The distance between the openings in the liquid inlet material may be 1.5 to 5.0 mm, or 1.5 to 2.5 mm. An advantage with a rather short distance between the openings is that the total open area will be high and the inlet rate will be fast.

The total open area of the openings in the horizontal plane of the inlet material in the central region is 40 to 70% of the total area in the horizontal plane of the inlet material in the central region.

The slits may have a slit length between 5.0 to 20.0 mm, 7.0 to 20 mm, 10.0 to 20.0. By having a slit length that is at least 5 mm, or at least 7 mm, or at least 10.0 mm the urine will reach the absorbent core below the inlet material more easily.

The absorbent product may have a narrower width in the crotch part and may be broader in the end parts. The reason for this is to shape the product to optimizing the fit to the body during use. However, it may be advantageous for process reasons to have the central region of the inlet material located substantially parallel to a longitudinal center line in the longitudinal direction of the absorbent product and not following the outer contour of the absorbent product.

The slits may be provided in staggered rows extending in the transversal direction of the absorbent product and has a slit distance B between the ends of two mutually sequential slits in the staggered row, a slit length A, and a row distance C between two adjacent rows.

The inlet material and the layer directly beneath the inlet material may have different color. This is an advantage since the plurality of openings will be visualized more distinct. For example, the inlet material may be colored or a layer between the inlet material and the absorbent core may be colored. A layer between the inlet material and the absorbent core may for example be a nonwoven. If the absorbent core/or part of the absorbent core has a shape with a less extension than the inlet material it may be an advantage if a material layer directly beneath the inlet material is colored since the less extension of the absorbent core beneath the colored layer will not so easily be recognized by the user.

The absorbent product may be an incontinence shield. The slit openings in the central region and the slit free edge regions improve the urine inlet rate as well as the bowl shape, which is especially advantageous for this kind of absorbent products.

The length of the inlet material in the longitudinal direction of the absorbent product may be 20 to 80% of the absorbent product in the longitudinal direction.

The absorbent product has a front end part and a back end part and a crotch part located between the front end part and the back end part.

The length of the front end part in its longitudinal direction of the absorbent product may be shorter than the length of the back end part in the longitudinal direction of the absorbent product.

The length of the back end part in its longitudinal direction of the absorbent product may be shorter than the length of the front end part in the longitudinal direction of the absorbent product.

The total length of the incontinence shield may be 15 to 50 cm. The total length of the incontinence shield may be less than 50 cm, or less than 30 cm.

The length of the inlet material in the longitudinal direction of the incontinence shield may be 20 to 80% of the total length of the incontinence shield in the longitudinal direction.

BRIEF DESCRIPTION OF FIGURES

FIG. 3 shows the incontinence shield of FIG. 2, seen from the side which will be facing the user when it is worn.

FIG. 4 also shows the incontinence shield of FIG. 2, seen from the side which will be facing the user when it is worn.

DETAILED DESCRIPTION OF THE FIGURES

Figure 1A:
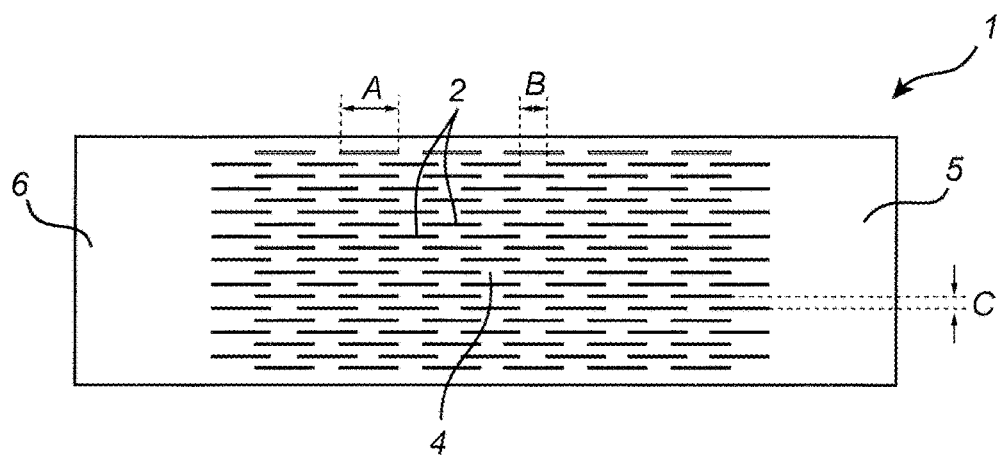
FIG. 1A shows a top view of a slit inlet material according to an embodiment of the invention before it has been expanded.

Embodiments of the invention will now be described by means of examples referring to FIGS. 1A-B and FIGS. 2-4. FIG. 1A shows a top view of a slit inlet material according to an embodiment of the invention before it has been expanded. FIG. 1A shows a top view of the inlet material 1 after provision of transversal slits 2. The slits 2 in FIG. 1A are straight, but may have any suitable shape such as for example wave-shaped. The slits 2 are provided in staggered rows extending in the transversal direction of the inlet material 1 having a slit length A and a slit distance B between the ends of two mutually sequential slits in the staggered row, and a row distance C between two adjacent rows. The inlet material 1 has in its transversal direction a central region 4 with slits and two edge regions 5, 6 without slits.

Figure 1B:
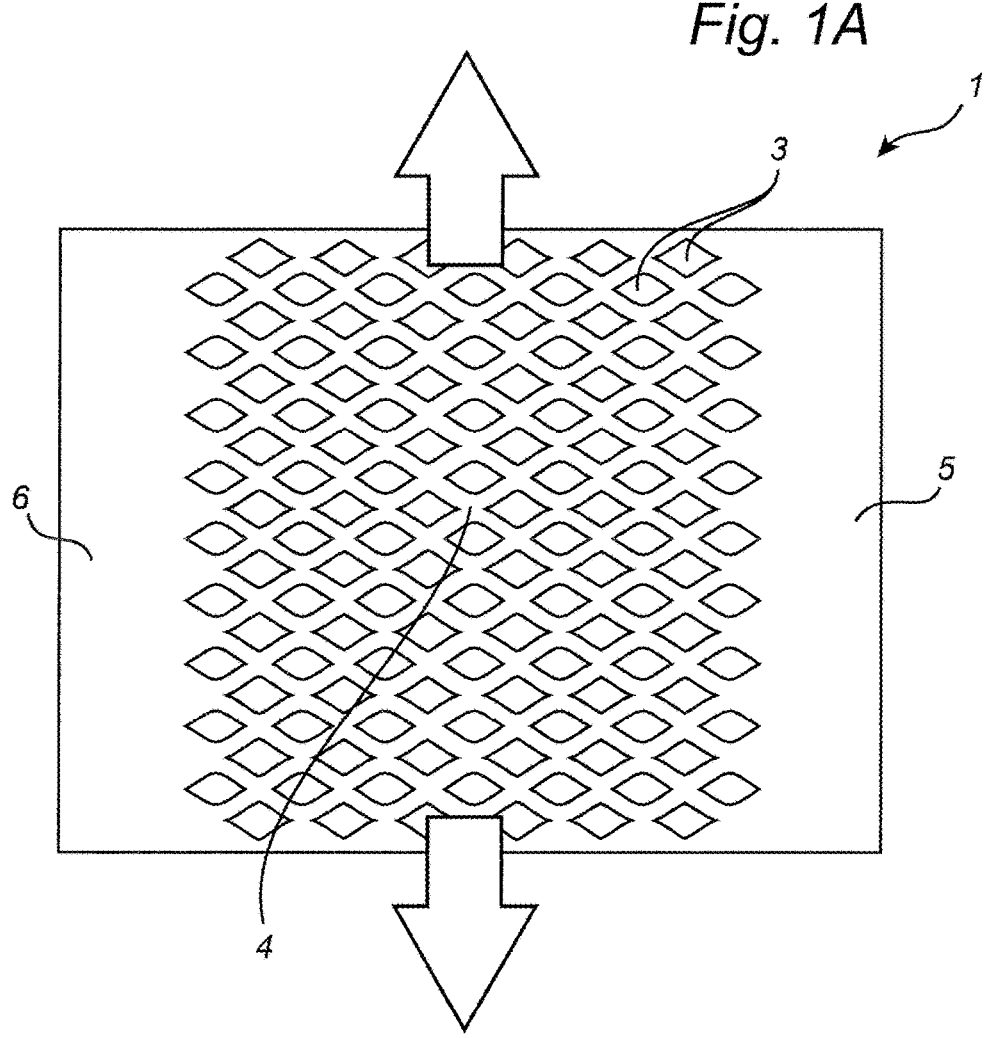
FIG. 1B shows a top view of the inlet material according to FIG. 1A after it has been expanded, i.e. after the slits have been opened to form openings.

FIG. 1B shows a top view of the inlet material 1 according to FIG. 1A after it has been expanded in the direction transversal to the slit 2 direction, i.e. after the slits 2 have been opened to form openings 3.

Figure 2:
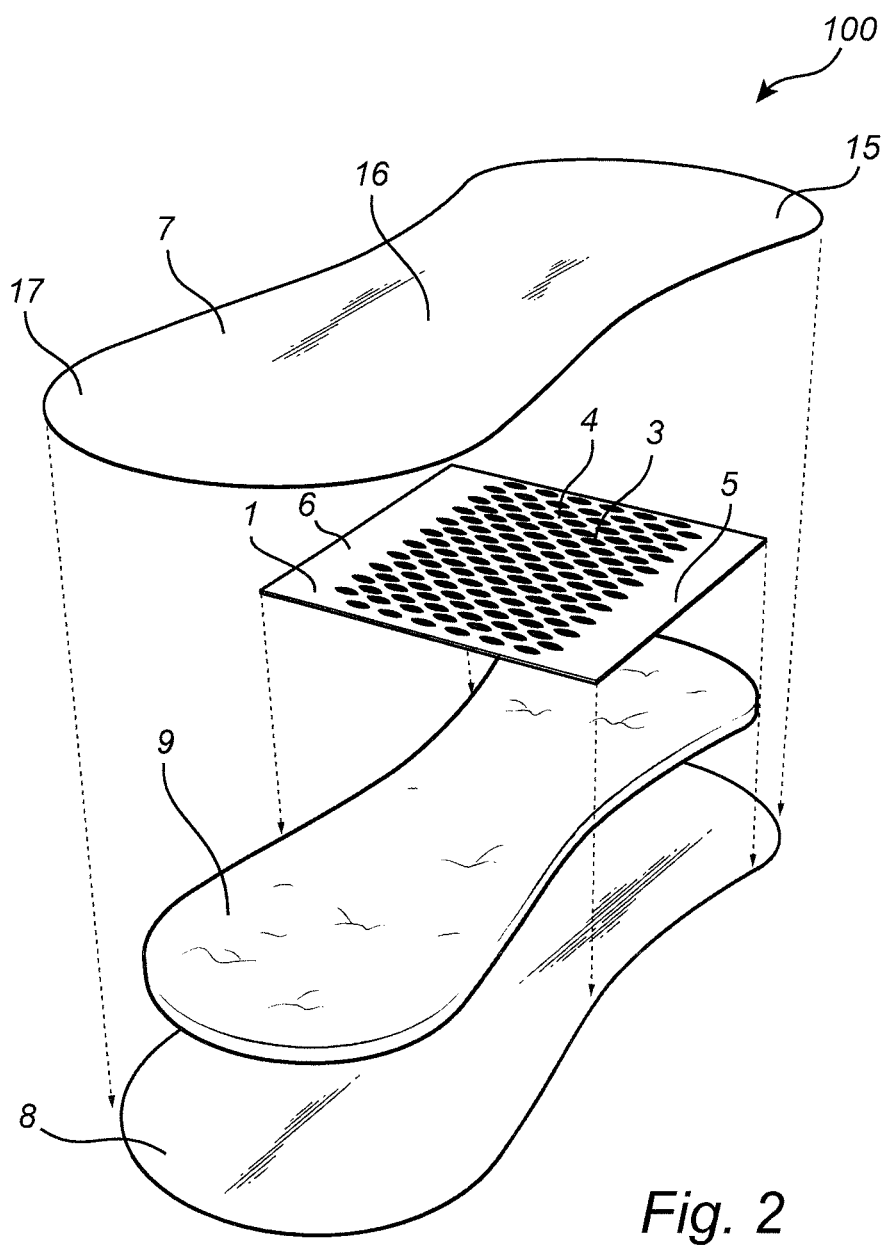
FIG. 2 shows a cross-sectional view of an incontinence shield according to an embodiment of the invention.

FIG. 2 shows a cross-sectional view of the different layers in the incontinence shield according to an embodiment of the invention. The incontinence shield 100 includes a liquid permeable topsheet 7, a liquid impermeable backsheet 8, and an absorbent core 9 enclosed between the topsheet 7 and the backsheet 8, and an inlet material 1 arranged between the topsheet 7 and the absorbent core 9. The incontinence shield 100 has in its longitudinal direction a front end part 15, a back end part 17 and a crotch part 16 intermediate the front end part 15 and the back end part 17. The inlet material 1 is located in the crotch part 16 of the product and the length of the front end part 15 in its longitudinal direction of the incontinence shield 100 is shorter than the length of the back end part 17 in the longitudinal direction of the incontinence shield 100. The crotch part 16 is a portion which is intended to be placed against the crotch of a wearer during use of the product and to constitute the main acquisition area for body fluid that reaches the incontinence shield 100.

The topsheet 7 and the backsheet 8 of the incontinence shield 100 extend together laterally outside of the absorbent core 9 along the whole circumference of the absorbent core 9. The topsheet 7 includes any material which is suitable for the purpose, i.e. soft and liquid pervious. Examples of commonly found topsheet 7 materials are nonwoven materials, perforated plastic films, plastic or textile mesh, and fluid permeable foam layers. Laminates include two or more topsheet materials are also commonly employed, as are top sheets including different materials within different parts of the fluid permeable wearer-facing surface.

The backsheet 8 is fluid impermeable. However, backsheet materials that are only fluid repellant may be used particularly in instances where relatively small amounts of urine are expected to be taken up. The backsheet 8 is commonly constituted by a thin, flexible, fluid-impermeable plastic film, but fluid-impermeable nonwoven materials, fluid impermeable foams and fluid impermeable laminates are also contemplated within the scope of the invention. The backsheet 8 may be breathable, implying that air and/or vapor may pass through the backsheet 8. Furthermore, the backsheet 8 may have an outer, garment-facing surface of a textile material such as nonwoven.

The absorbent core 9 may be made up of any suitable absorbent or fluid uptake material as known in the art, such as one or more layers of cellulose fluff pulp, foam, fibre waddings, etc. The absorbent core 9 may contain fibers or particles of highly absorbent polymer material, commonly known as superabsorbents, which are materials having the ability to absorb and retain large quantities of fluid upon formation of a hydrogel. The superabsorbents may be mixed with cellulose fluff pulp and/or may be arranged in pockets or layers in the absorbent core 9. The fibres may be pulp fibres and the superabsorbent material may be polyacrylate-based particles. The absorbent core 9 may further incorporate components for improving the properties of the absorbent core 9. Some examples of such components are binder fibers, fluid-dispersing materials, wetness indicators etc., as known in the art. The incontinence shield 100 has an elongate, generally rectangular shape when fully extended in all directions. Any suitable shape may be used for the absorbent product, such as hourglass shape, trapezoidal shape, etc. The incontinence shield has a transversal rear end edge 14 intended to be orientated rearwards during use of the absorbent article, and a front end edge 13 intended to be facing forwards towards the abdomen of the wearer. The incontinence shield 100 may further include fastening means for fastening of the absorbent product inside a supporting pant garment, such as a pair of underpants. The fastening means may be in the form of two longitudinally extending bands of pressure sensitive adhesive arranged on the garment-facing surface of the backsheet 8. The fastening means can be covered by a releasable protective layer, e.g. a siliconized paper, a nonwoven or any other releasable material as is known in the art. Before placing the absorbent product in the supporting pant garment, the protective layer is removed from the fastening means to expose the adhesive and make it available for fastening to the pant garment.

The fastening means is optional and may be omitted, if desired. When using an adhesive fastening means, any suitable adhesive pattern may be used such as full coating of the backsheet, one or more longitudinal adhesive band, transverse bands, dots, circles, curves, stars, etc.

The inlet material 1 in FIG. 2 is situated above the absorbent core 9 and beneath and in direct contact with the topsheet 7. The absorbent core 9 of the incontinence shield 100 includes one absorbent layer, but the absorbent core 9 may also include two or more absorbent layers. The absorbent core 9 may be homogeneous structures or may in themselves be layered structures such as absorbent laminates of the same or different materials. The absorbent layers may have uniform thickness or may vary in thickness in different parts of the layers. Similarly, the basis weight and composition may vary within the absorbent layers. By way of example, an absorbent layer may include a mixture of absorbent and/or non-absorbent fibers and superabsorbent material, wherein the ratio of superabsorbent material to fibers may vary in the layer. The absorbent core 9 may have any suitable shape, such as an hourglass shape with widened end portions and a narrow portion in the crotch portion, or a rectangular shape. The inlet material 1 in the incontinence shield illustrated in FIGS. 2-4 has a rectangular shape.

FIG. 3 shows the incontinence shield of FIG. 2, seen from the side which will be facing the user when it is worn. In FIG. 3, the edge regions 5, 6 of the inlet material 1 is forming the leg elastics 18, 19. The edge regions 5, 6 have a greater elasticity than the central region 4 of the inlet material 1 and functions as leg elastics 18,19. The leg elastics 18,19 are the edge regions 5,6 of the inlet material 1. FIG. 4 also shows the incontinence shield (100) of FIG. 2, seen from the side which will be facing the user when it is worn. In FIG. 4, the bowl shape of the incontinence shield 100 formed by the elastic contraction of the edge regions 5,6 of the inlet material 1 is illustrated. The incontinence shield 100 described in FIGS. 2-4 is only one illustration of an absorbent product suitable for the present invention.

The invention claimed is:

1. An absorbent product having in its longitudinal direction a crotch part and two end parts comprising:
a liquid pervious topsheet;
a liquid impervious backsheet;
an absorbent core enclosed between the liquid pervious topsheet and liquid impervious backsheet; and
an inlet material having a plurality of openings located in at least the crotch part, wherein the plurality of openings in the inlet material are formed from a plurality of slits extending in the transversal direction of the absorbent product by expanding the continuous inlet material in the longitudinal direction of the absorbent product, and wherein the liquid inlet material in the transversal direction of the absorbent product has a central region and two edge regions and the plurality of openings are located in the central region, wherein both edge regions are free of openings so that the central region of the inlet material with the plurality of openings has a lesser degree of elasticity than the edge regions.

2. The absorbent product according to claim 1, wherein the edge regions of the inlet material has a greater elasticity than the central region of the inlet material.

3. The absorbent product according to claim 2, wherein the crotch part has a bowl shape.

4. The absorbent product according to claim 1, wherein the inlet material is located in the crotch part only.

5. The absorbent product according to claim 1, wherein the inlet material is located between the top sheet and the absorbent core.

6. The absorbent product according to claim 1, wherein the inlet material is the liquid permeable top sheet or part thereof.

7. The absorbent product according to claim 5, wherein the inlet material, at least in the crotch part, has a greater width than the absorbent core.

8. The absorbent product according to claim 7, wherein the central region of the inlet material, at least in the crotch part, also has a greater width than the absorbent core.

9. The absorbent product according to claim 5, wherein the liquid pervious topsheet and the liquid impervious backsheet have substantially same or greater width in the crotch part than the inlet material.

10. The absorbent product according to claim 1, wherein the edge regions have a width that is of least 5.0 mm.

11. The absorbent product according to claim 1, wherein the length of the openings in the transversal direction of the absorbent product are 5.0 to 20.0 mm.

12. The absorbent product according to claim 1, wherein the width of the openings in the longitudinal direction of the absorbent product is 0.2 to 3.0 of the length of the opening in the transversal direction.

13. The absorbent product according to claim 1, wherein the inlet material has been extended 30% to 200% from the original length of the unexpanded inlet material.

14. The absorbent product according to claim 1, wherein the inlet material is hydrophobic.

15. The absorbent product according to claim 1, wherein the inlet material is a foam material.

16. The absorbent product according to claim 1, wherein the inlet material is a nonwoven.

17. The absorbent product according to claim 1, wherein the distance between the openings are 1.5 to 5.0 mm.

18. The absorbent product according to claim 1, wherein the total open area in the horizontal plane of the product formed by the plurality openings in the central region is 40% to 70% of the total area in the horizontal plane in the central region.

19. The absorbent product according to claim 1, wherein the inlet material and a layer directly below the inlet material have different colors.

20. An incontinence shield comprises the absorbent product according to claim 1.

21. The incontinence shield according to claim 20, wherein the length of the inlet material in the longitudinal direction of the incontinence shield is 20 to 80% of the total length of the incontinence shield in the longitudinal direction.

22. The incontinence shield according to claim 20, wherein the incontinence shield is less than 50 cm in its longitudinal direction.

23. The absorbent product according to claim 1, wherein the plurality of openings are not present in the two edge regions.

* * * * *